(12) United States Patent
Kim et al.

(10) Patent No.: US 10,335,488 B2
(45) Date of Patent: Jul. 2, 2019

(54) METHOD FOR TREATING CANCER BY PHOTODYNAMIC THERAPY

(71) Applicant: D. R. NANO CO., LTD., Seoul (KR)

(72) Inventors: Sehoon Kim, Seoul (KR); Ick Chan Kwon, Seoul (KR); Sangyoup Lee, Seoul (KR)

(73) Assignee: D. R. NANO CO., LTD., Seoul (KR)

( * ) Notice: Subject to any disclaimer, the term of this patent is extended or adjusted under 35 U.S.C. 154(b) by 0 days.

(21) Appl. No.: 16/109,670

(22) Filed: Aug. 22, 2018

(65) Prior Publication Data

US 2019/0000974 A1    Jan. 3, 2019

Related U.S. Application Data

(63) Continuation-in-part of application No. 14/667,935, filed on Mar. 25, 2015, now Pat. No. 10,086,075.

(30) Foreign Application Priority Data

Mar. 26, 2014 (KR) .................. 10-2014-0035407

(51) Int. Cl.

| A61B 8/00 | (2006.01) |
|---|---|
| A61K 41/00 | (2006.01) |
| A61K 49/00 | (2006.01) |
| A61K 9/51 | (2006.01) |
| A61K 9/00 | (2006.01) |
| A61P 35/00 | (2006.01) |
| A61K 47/32 | (2006.01) |
| A61K 47/54 | (2017.01) |

(52) U.S. Cl.
CPC ........ *A61K 41/0057* (2013.01); *A61K 9/0019* (2013.01); *A61K 9/5123* (2013.01); *A61K 9/5138* (2013.01); *A61K 47/32* (2013.01); *A61K 47/542* (2017.08); *A61K 49/003* (2013.01); *A61K 49/006* (2013.01); *A61K 49/0093* (2013.01); *A61P 35/00* (2018.01); *A61K 49/0082* (2013.01)

(58) Field of Classification Search
CPC .... A61K 9/0019; A61K 9/0024; A61K 9/113; A61K 9/127; A61K 9/1605; A61K 41/00; A61K 41/0019; A61K 41/0038; A61K 41/0057

See application file for complete search history.

(56) References Cited

U.S. PATENT DOCUMENTS

2011/0112059 A1* 5/2011 Hasan .................. C07D 501/52
                                                              514/209

OTHER PUBLICATIONS

Patel (Targeted methylene blue-containing polymeric nanoparticle formulations for oral antimicrobial photodynamic therapy, 2009, Pharmaceutical Science Master's Thesis http://hdl.handle.net/2047/d1001939x hereafter Patel). (Year:2009).*

* cited by examiner

*Primary Examiner* — Micah Paul Young
(74) *Attorney, Agent, or Firm* — STIP Law Group, LLC

(57) ABSTRACT

The present invention discloses a method for treating cancer disease by photodynamic therapy. The photodynamic therapy in the present invention uses a methylene blue nanoparticle as a therapeutic agent. The methylene blue nanoparticle of the present invention for use as a topical cancer targeting phototherapeutic agent is composed of only a material of which the composition is clinically used or derived from human bodies, and thus a nanopreparation in which a barrier to clinical entry is low and the possibility of commercialization is very high, exhibits near-infrared fluorescence along with cancer targeting property, capacity of generating a singlet oxygen and the like. Therefore, the methylene blue nanoparticle in the present invention is able to cure cancer cells by cell apoptosis in irradiation conditions.

10 Claims, 18 Drawing Sheets

[FIG. 1]
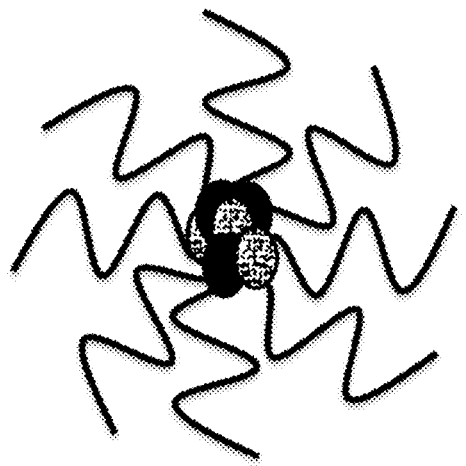 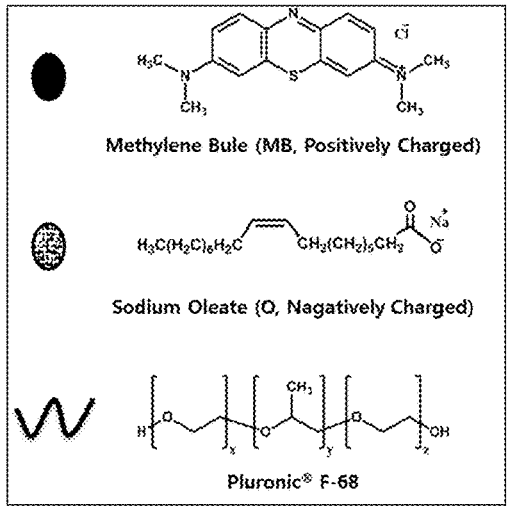
MB NPs (Charge complex NPs)
[FIG. 2a]
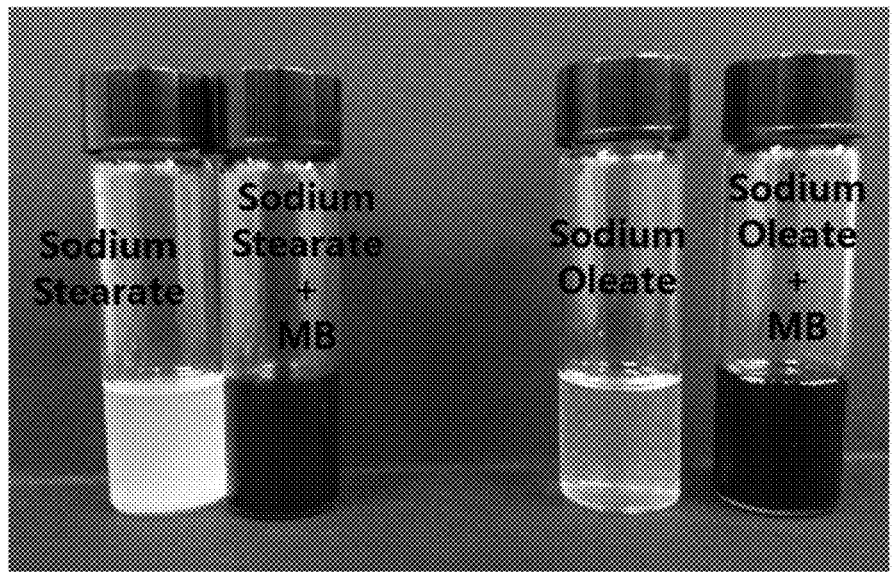

[FIG. 2b]
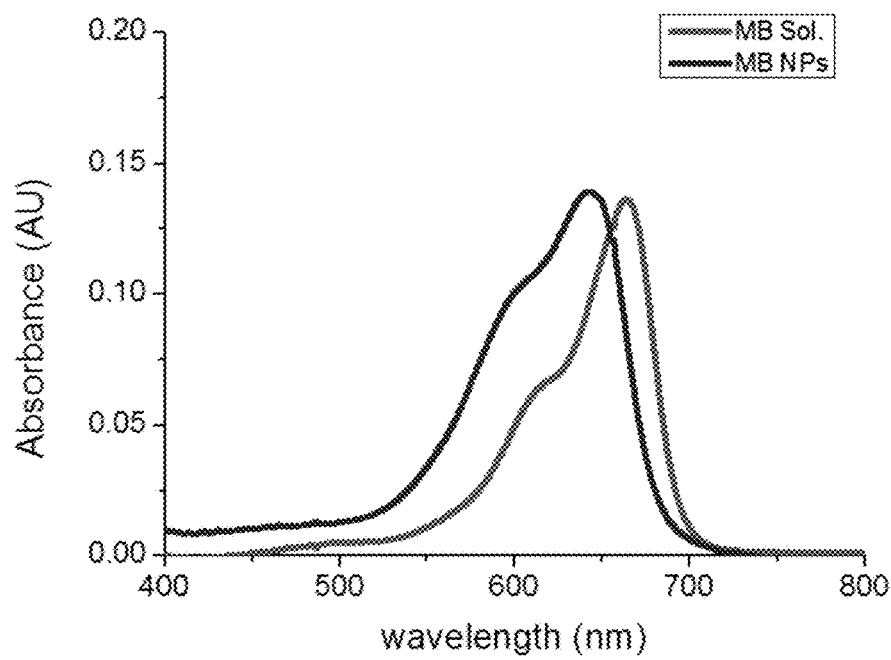
[FIG. 2c]
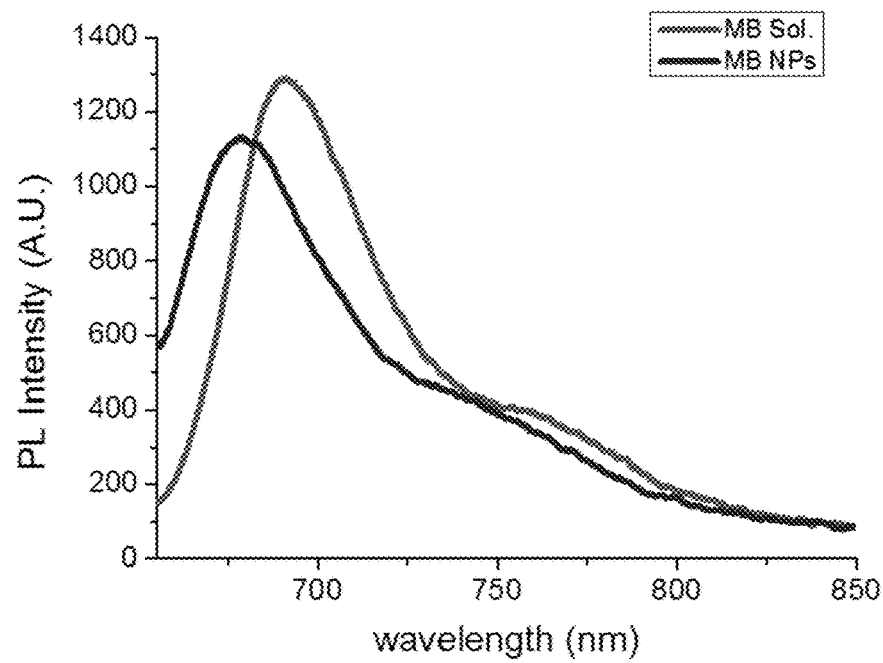

[FIG. 3a]
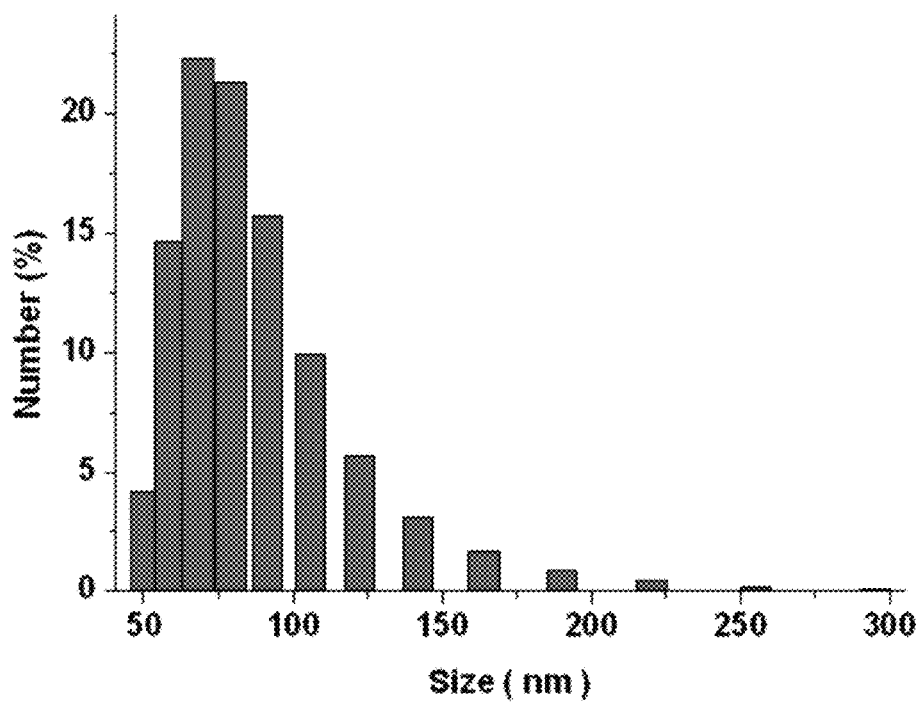
[FIG. 3b]
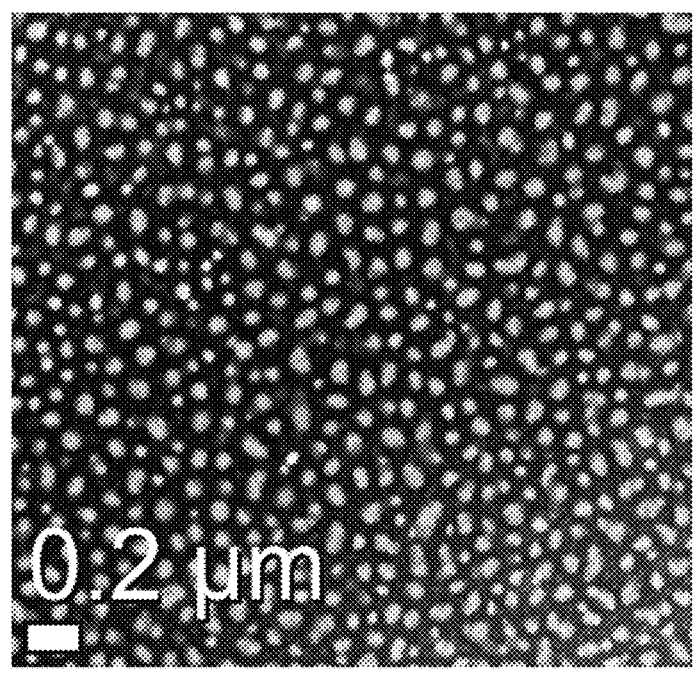

[FIG. 4]
|  | $\Phi_{SOG}$ |
|---|---|
| MB Sol. at RT | 0.65 |
| MB NPs at RT | 0.44 |
| MB Sol. at 37°C | 0.57 |
| MB NPs at 37°C | 0.63 |
[FIG. 5a]
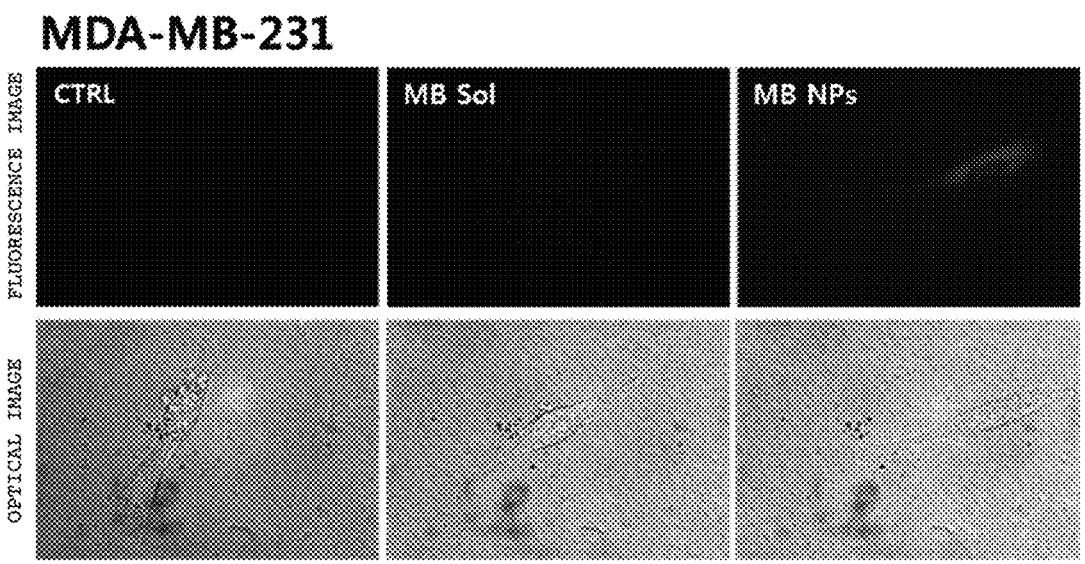

[FIG. 5b]
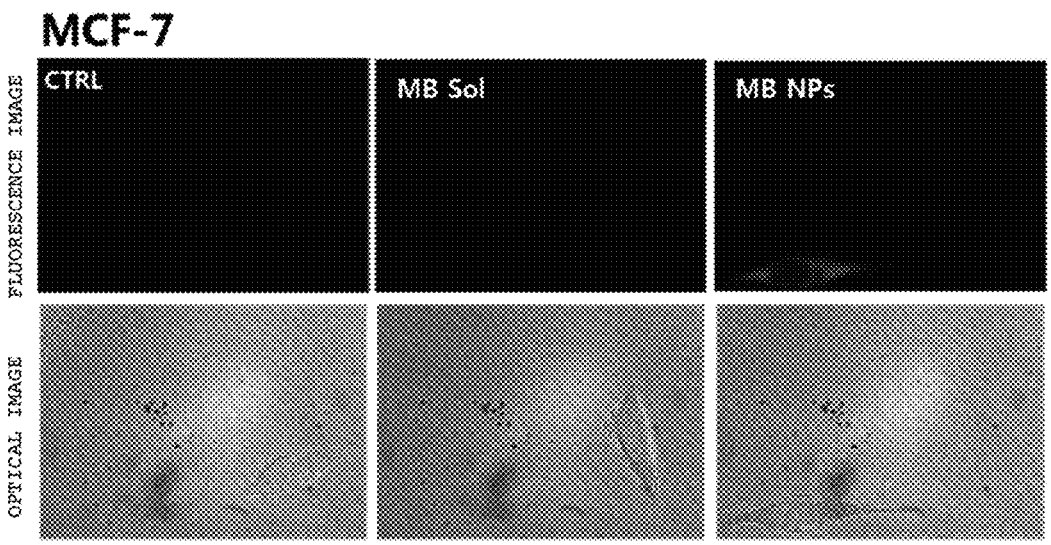
[FIG. 5c]
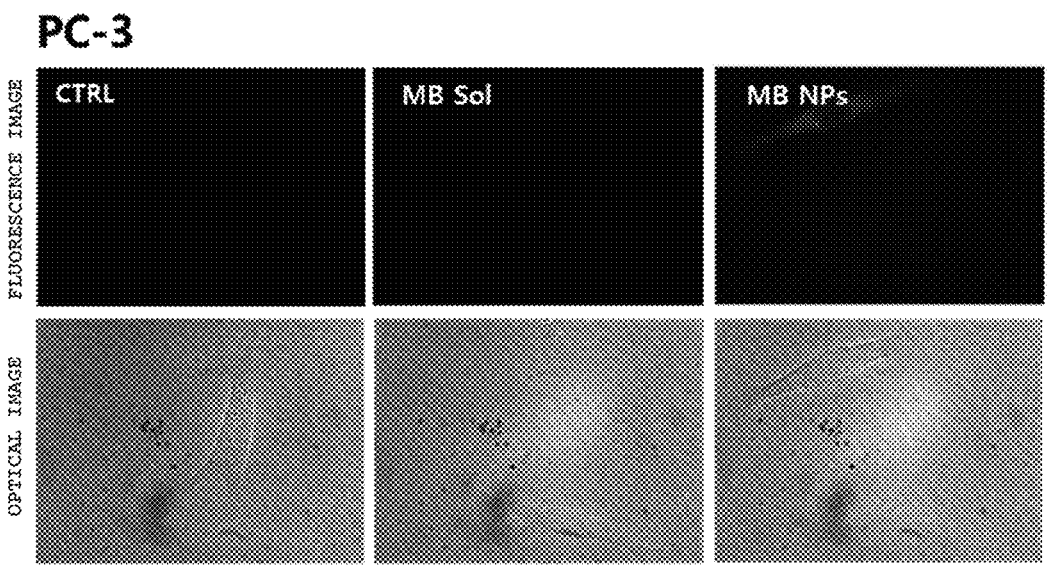

[FIG. 5d]
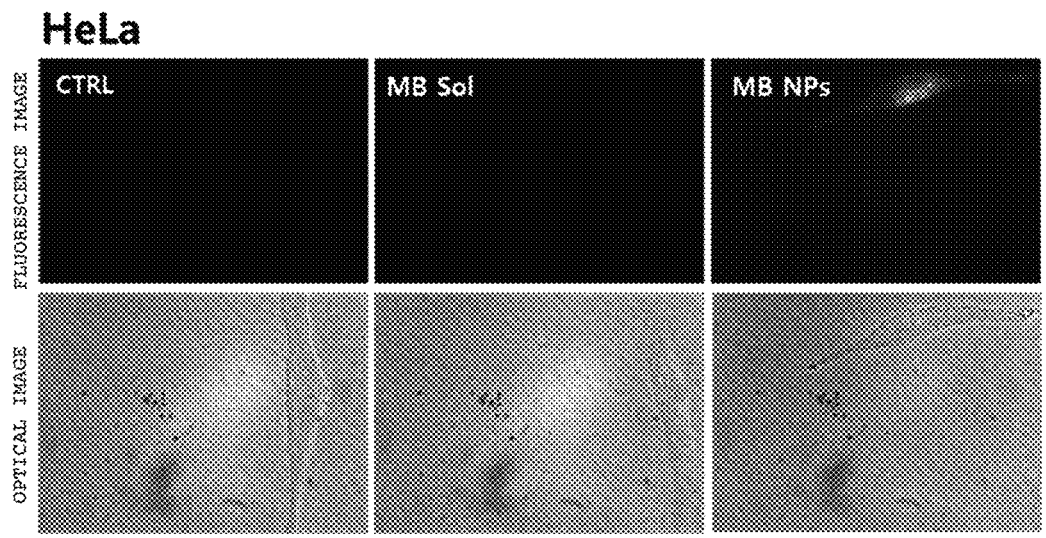
[FIG. 5e]
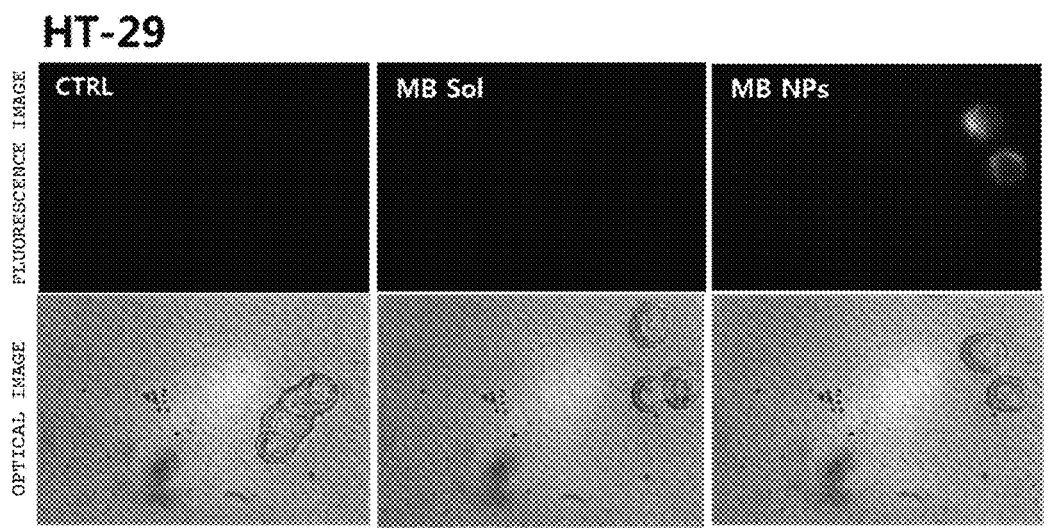

[FIG. 6a]
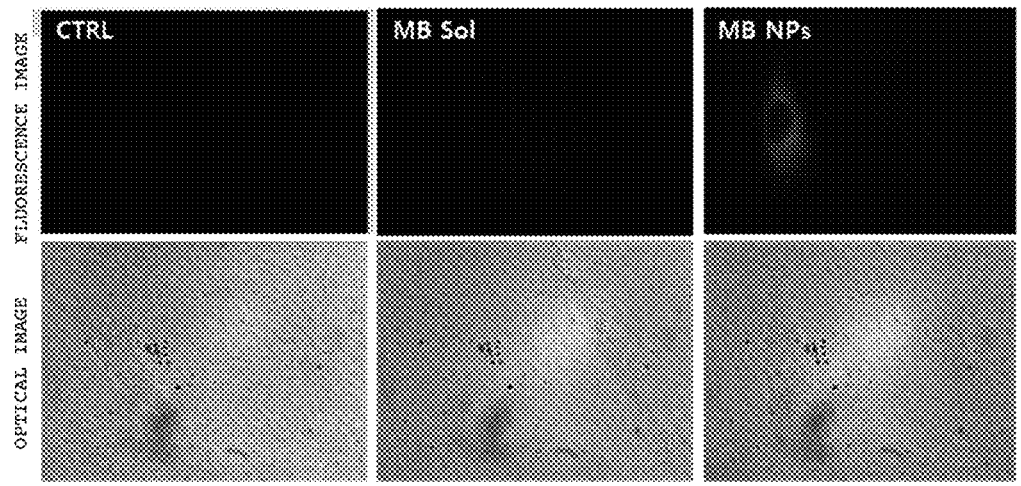
[FIG. 6b]
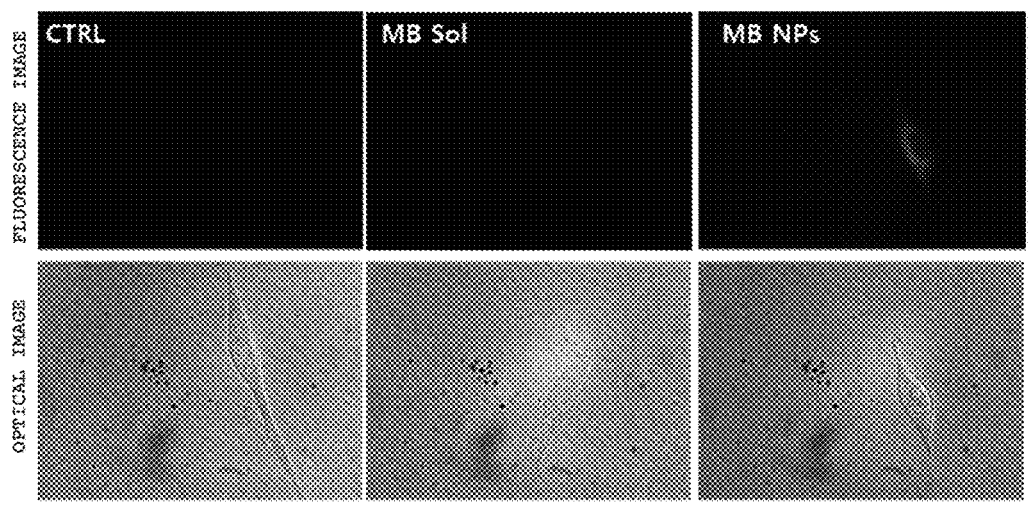

[FIG. 6c]
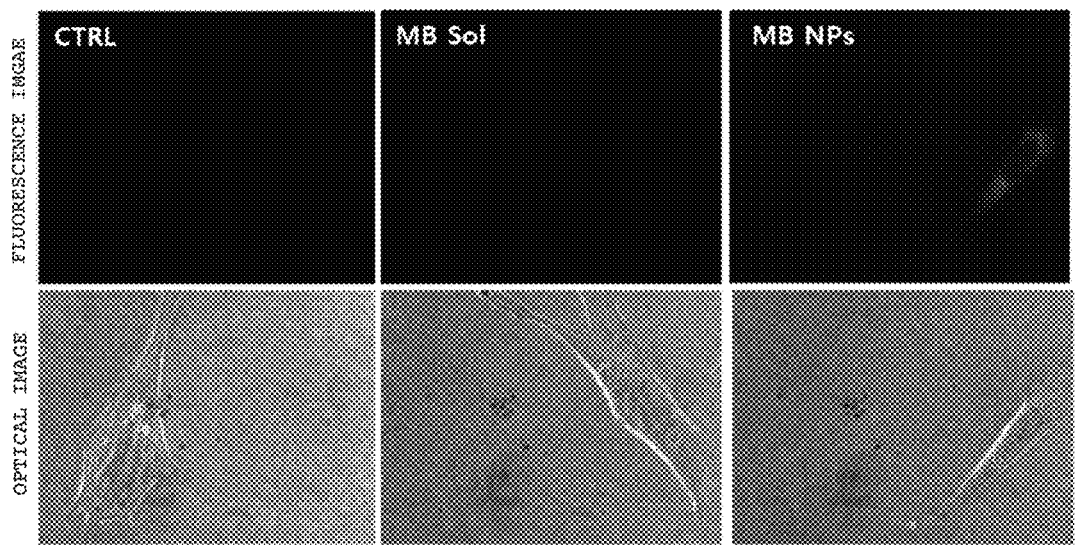
[FIG. 7a]
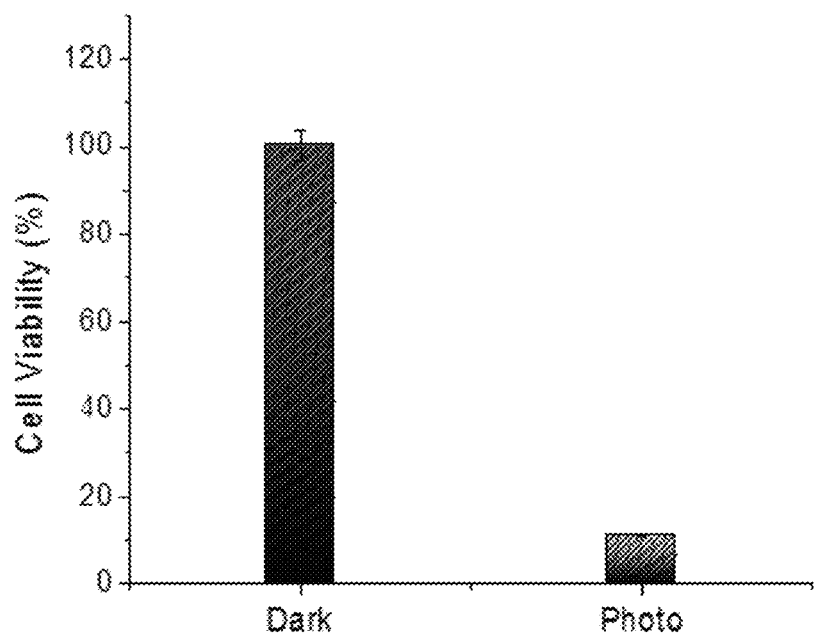

[FIG. 7b]
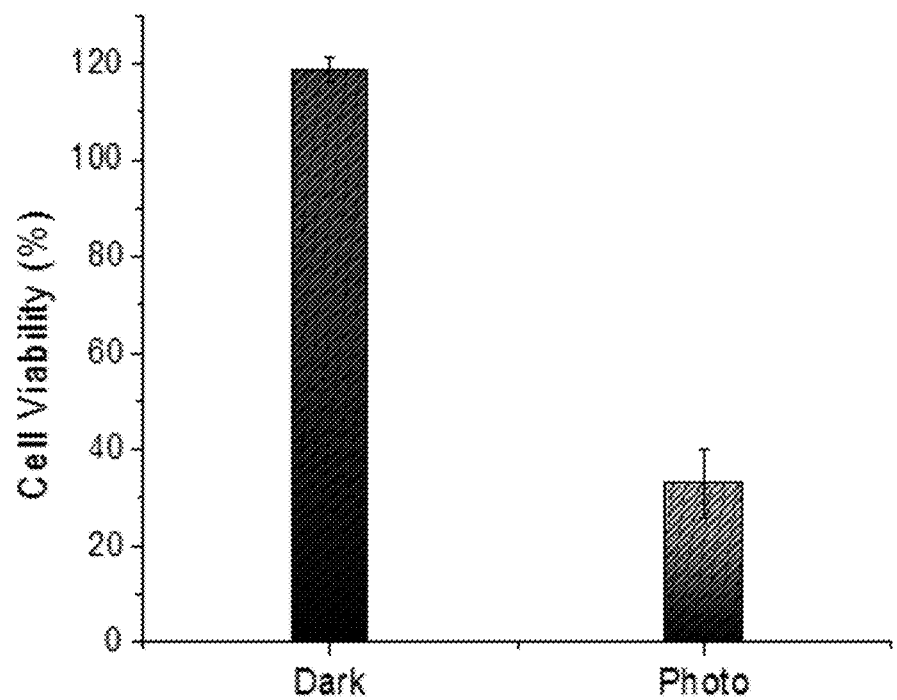
[FIG. 7c]
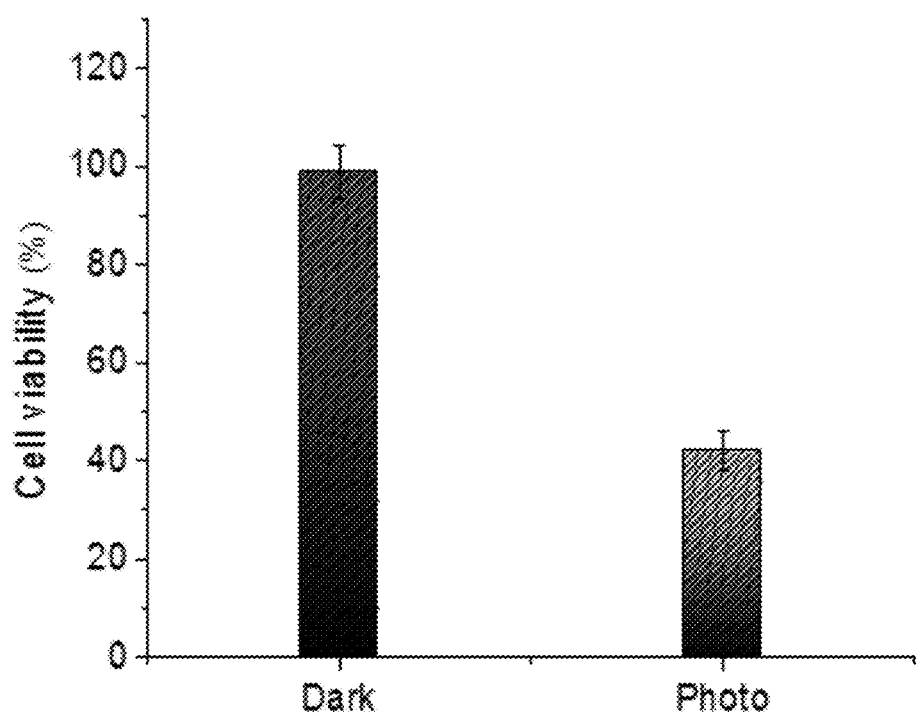

[FIG. 7d]
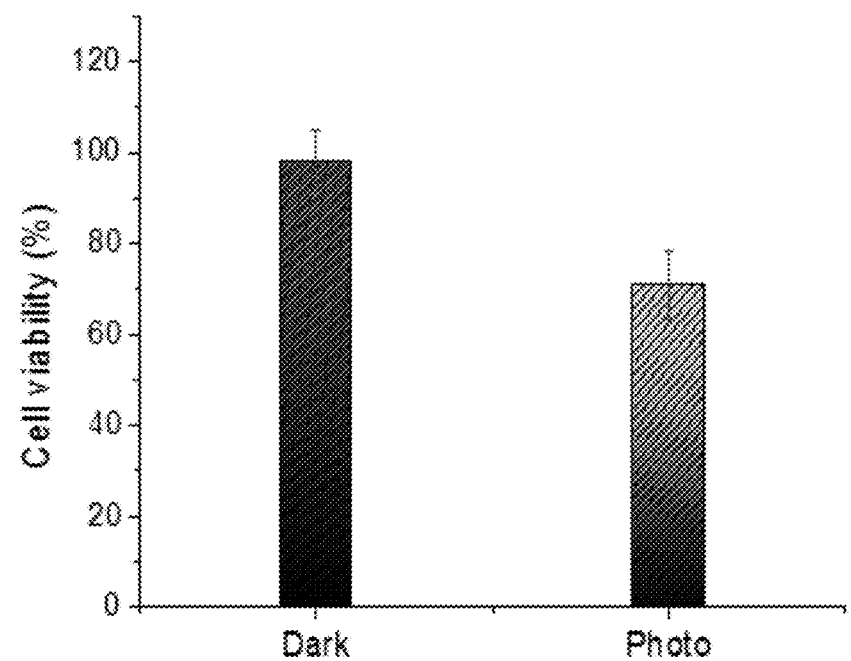
[FIG. 7e]
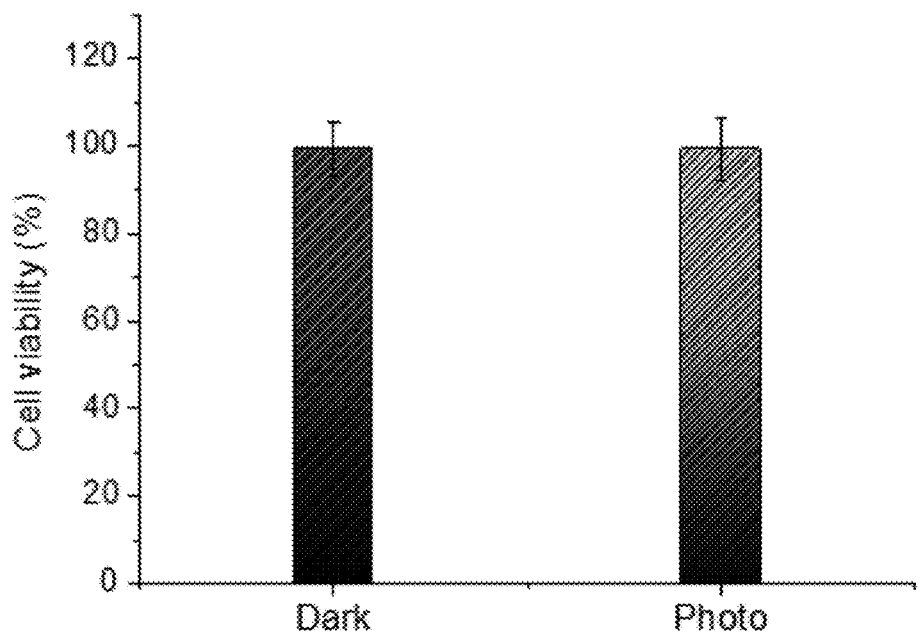

[FIG. 8a]
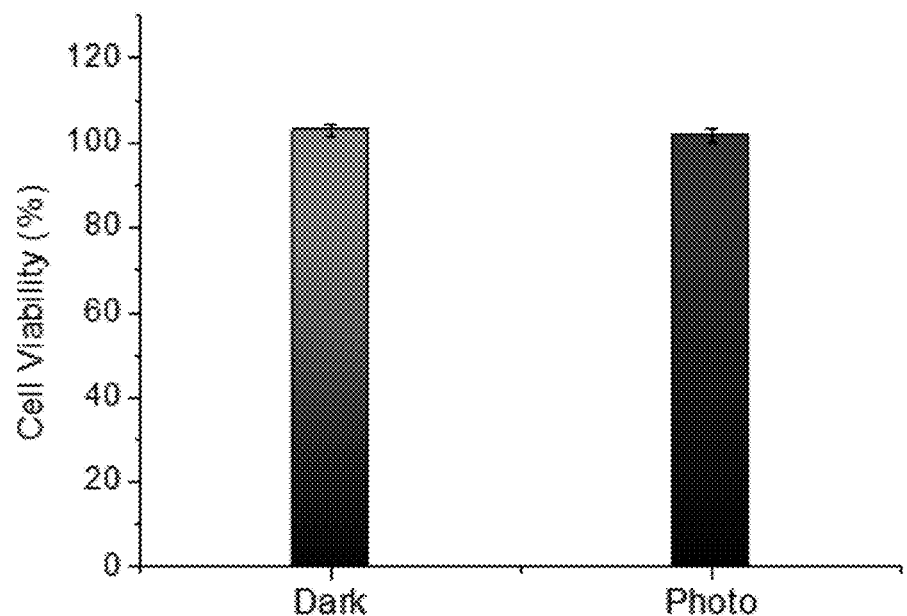
[FIG. 8b]
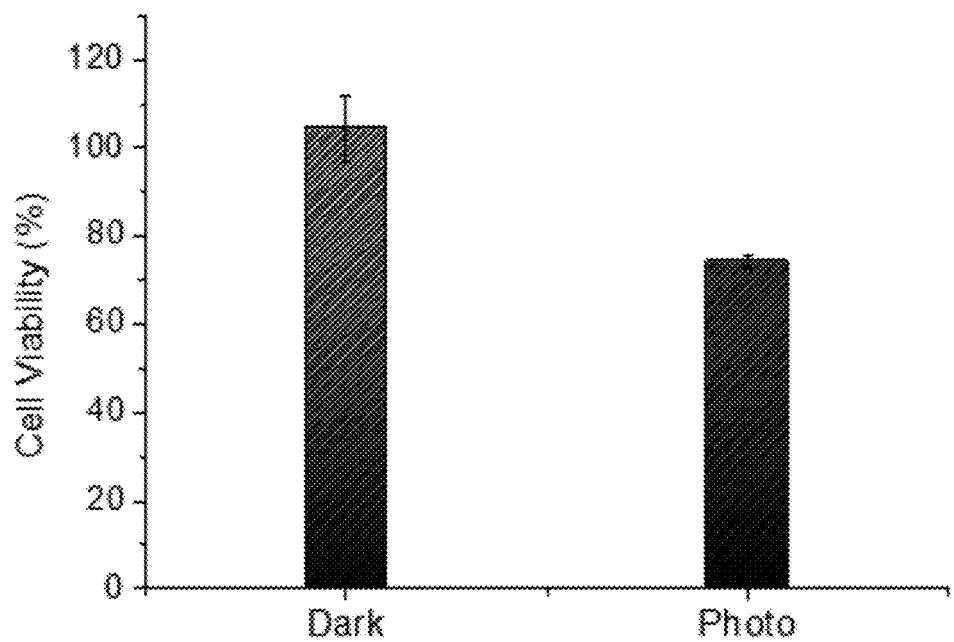

[FIG. 8c]
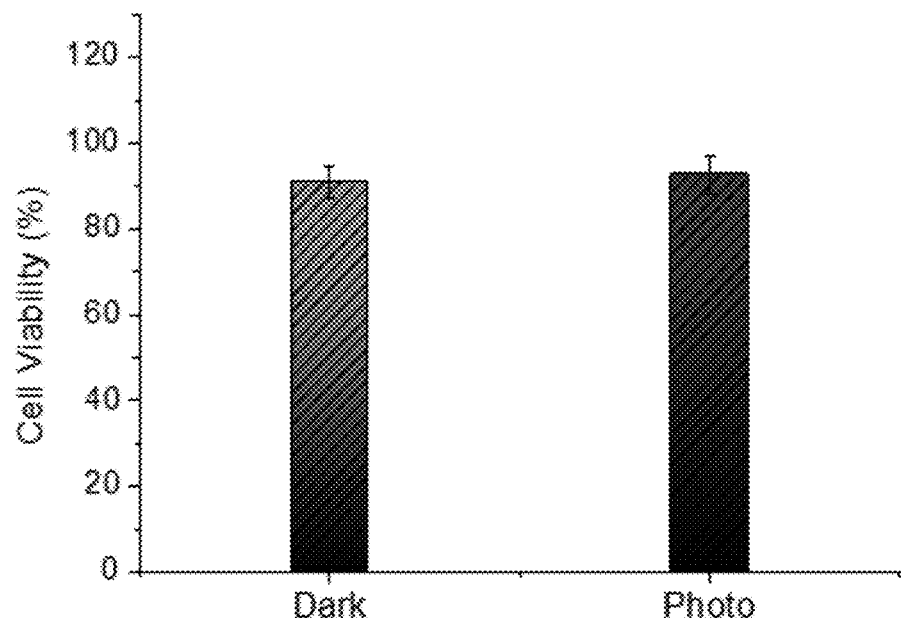
[FIG. 9]
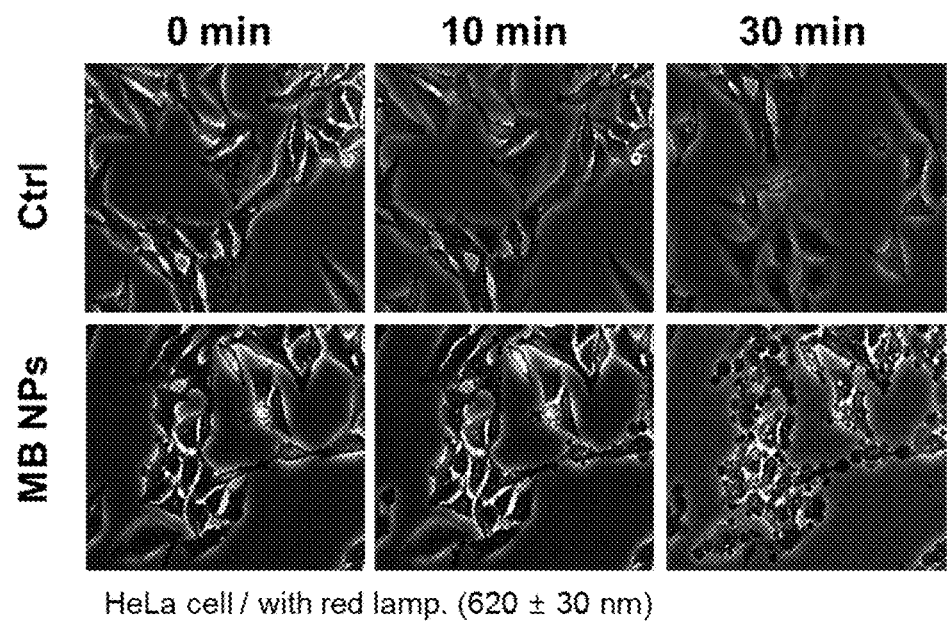
HeLa cell / with red lamp. (620 ± 30 nm)

[FIG. 10]
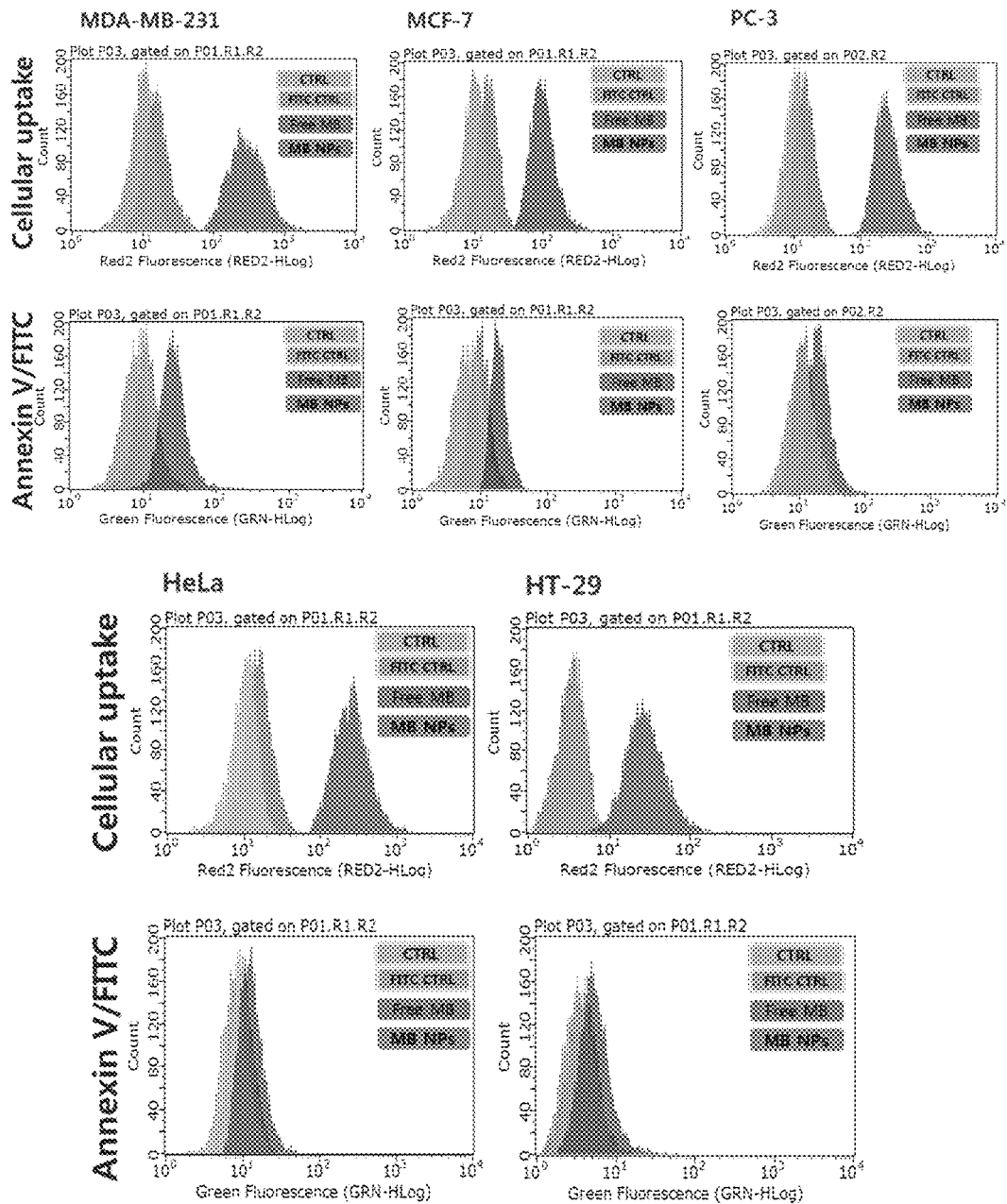

[FIG. 11]
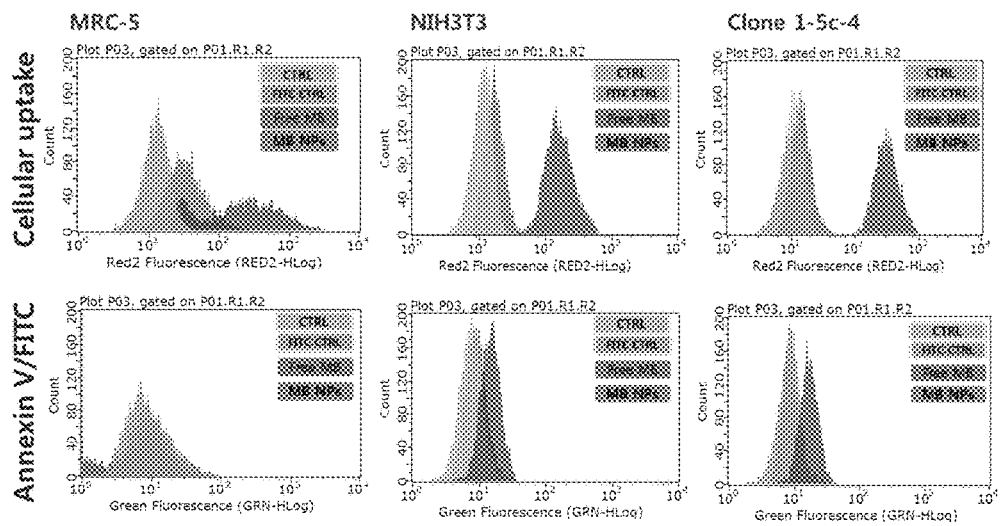
[FIG. 12]
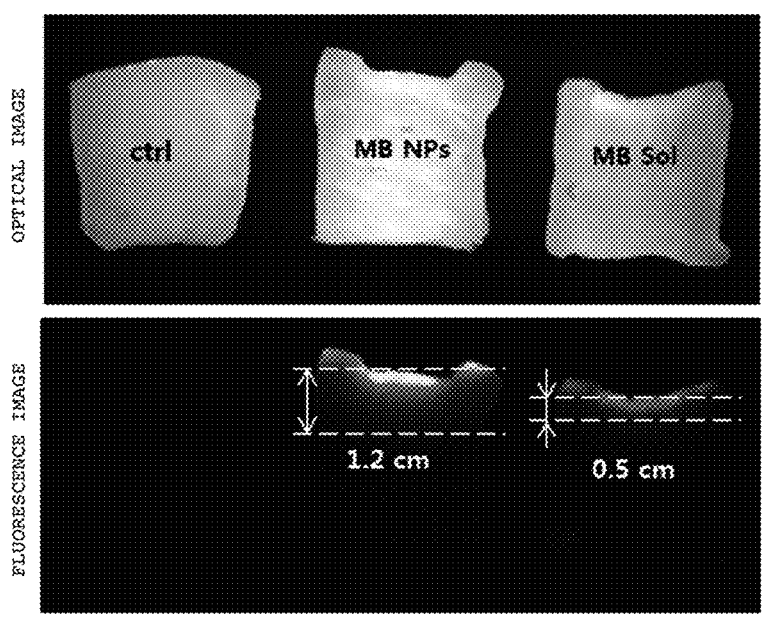

[FIG. 13a]
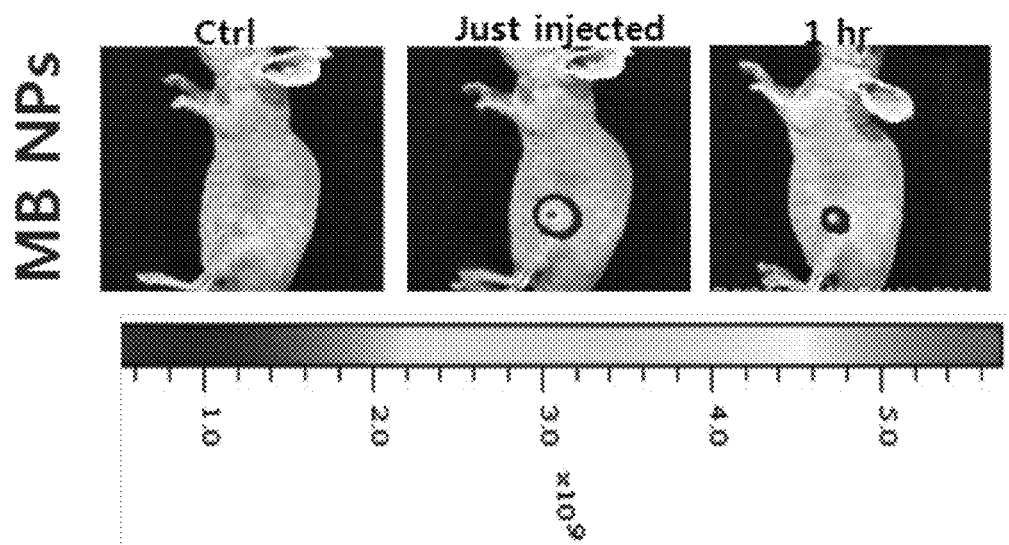
[FIG. 13b]
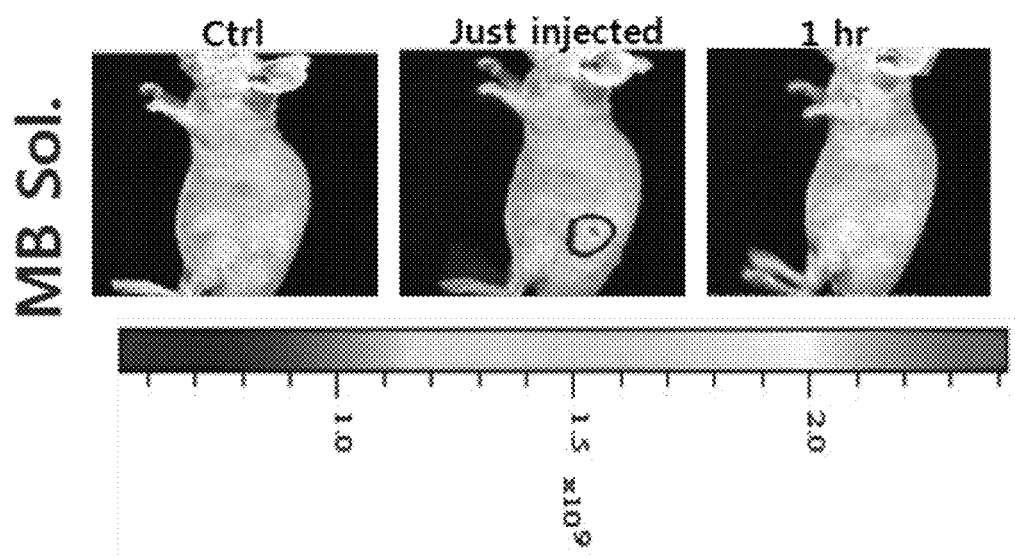

[FIG. 14]
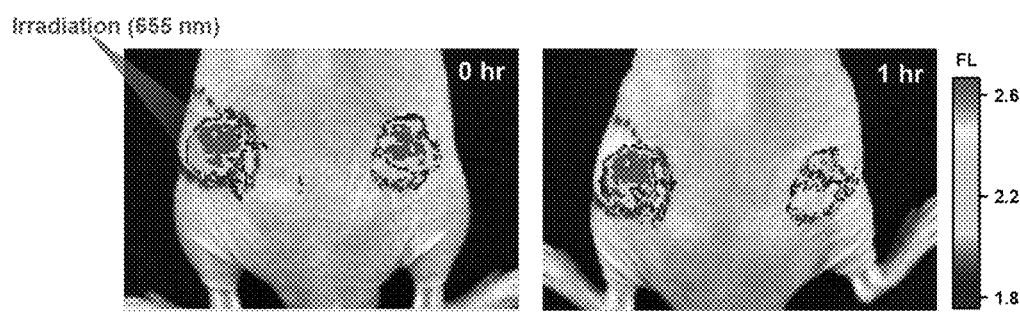
[FIG. 15a]
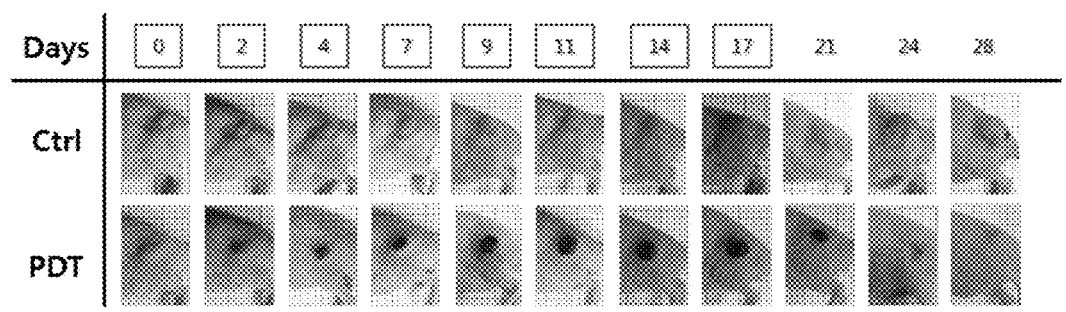

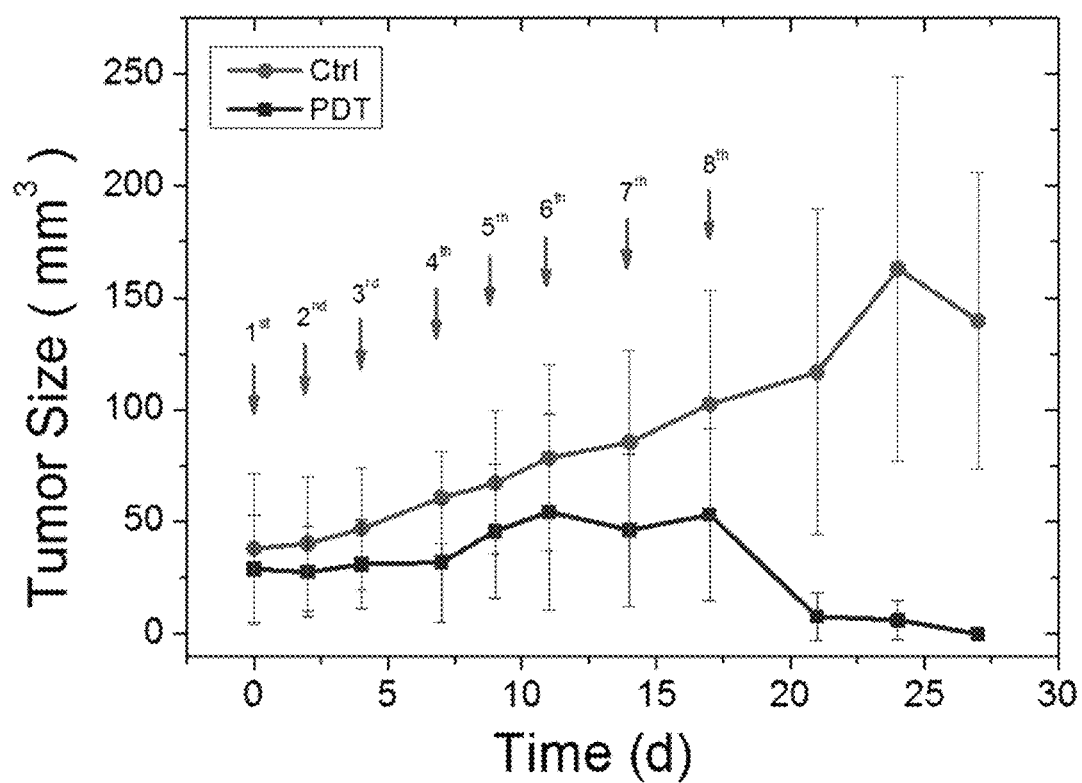
[FIG. 15b]

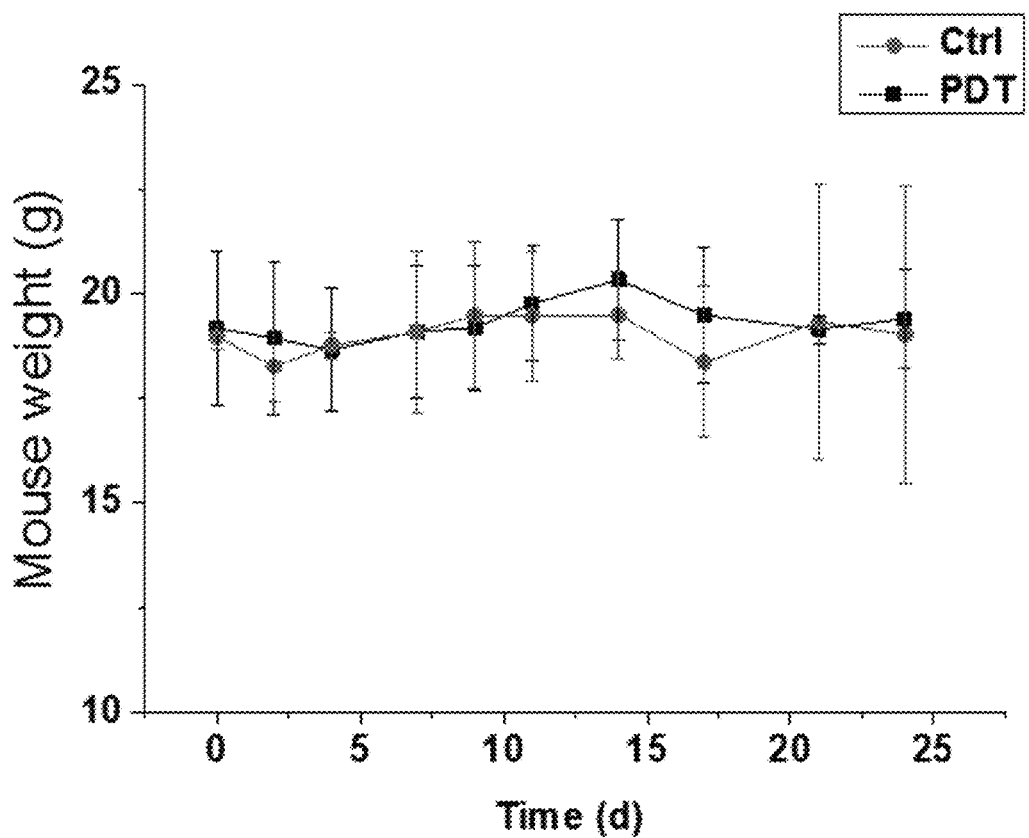
[FIG. 16]

METHOD FOR TREATING CANCER BY PHOTODYNAMIC THERAPY

CROSS-REFERENCE TO RELATED APPLICATIONS

This application is a Continuation-in-Part of application Ser. No. 14/667,935 filed on Mar. 25, 2015, which in turn claims the benefit of Korean Patent Application No. 10-2014-0035407 filed on Mar. 26, 2014, the disclosures of which are incorporated by reference into the present application.

BACKGROUND OF INVENTION

Field of Invention

The present invention discloses a method of using methylene blue nanoparticle for treating cancer disease by photodynamic therapy. The photodynamic therapy in the present invention uses a methylene blue nanoparticle as a therapeutic agent.

Background of Invention

The primary conventional therapies for treating cancer, cardiovascular, and ophthalmological diseases are a surgical operation, radiotherapy, and chemotherapy. Since the conventional therapies for treating cancer such as surgical operation, chemotherapy and radiotherapy have only limited treatment effects and may harm normal tissues as well as be causing severe side effects, new therapeutic methods such as targeted cancer therapies and photodynamic therapies have drawn attention. The basic concept of photodynamic therapy is the use of the principle that a photosensitizer exposed to light generates a singlet oxygen and other active oxygen species. Various photosensitizers have been developed in many countries such as the US and Japan and applied to various kinds of cancer therapies.

Most of the photosensitizers currently used in photodynamic therapy for cancer have disadvantages such as non-specific damage of normal tissues, decomposition into inactive forms, low solubility in vivo, inappropriate interactions with biomolecules, and aggregation among the photosensitizers, and thus show a particular limitation in cancer-specific delivery and low photosensitivity. Therefore, there is a need for an appropriate new delivery system in order to enhance the effects of the therapy.

Photosensitizers for effective treatment require in vivo stability, cancer targeting, low dark toxicity, long wavelength absorption for deep tissue penetration, and high photosensitivity.

Currently, photosensitizers available in Korea include first-generation porphyrin-based Photofrin (630 nm, Axcan, Canada) and Photogem (630 nm, Lomonosov Institute of Fine Chemicals, Russia), but these photosensitizers have a problem with a high supply price (about three million won) per operation.

In addition, although other various photosensitizers have been developed in other countries such as the US and Japan and applied to various kinds of cancer therapies, they still require much time and economic supports until their clinical use.

Meanwhile, methylene blue has been used for medical visualization of lymphatic vessels in a clinical operation such as excision of sentinel lymph nodes. Despite the use of the medical application, however, methylene blue has not been clinically used as a photo-therapeutic agent and a fluorescent cancer contrast agent with high efficiency.

SUMMARY OF INVENTION

The present inventors have tried to develop a therapeutic technology for photodynamic therapy with bioimaging using methylene blue which has been used for a clinical purpose other than conventional fluorescent contrast and phototherapy. As a result, the present inventors have successfully prepared self-assembled nanoparticles in a water system with high topical cancer targeting, composed of clinically available materials and compounds derived from human bodies.

Therefore, an object of the present invention is to provide a method of using a methylene blue nanoparticle for treating cancer disease by bioimaging and photodynamic therapy.

The present invention is related to a method of using methylene blue nanoparticle for treating cancer and the method includes the steps of; i) administrating therapeutic agents containing the methylene blue nanoparticles into a tissue, ii) applying light irradiation to the tissue, iii) generating a singlet oxygen from the methylene blue nanoparticles and iv) inducing cell apoptosis and reducing the cancer area.

In the method the methylene blue nanoparticle comprises a methylene blue-fatty acid complex and an amphiphilic copolymer of pluronic F-68 which comprises a polyoxyethylenepolyoxypropylene-polyoxyethylene block copolymer, wherein the said methylene blue-fatty acid complex is enclosed in a micelle formed by the amphiphilic copolymer, and wherein the methylene blue nanoparticle has a diameter of 80 to 100 nm and is self-assembled in an aqueous environment.

Furthermore, the administrating the therapeutic agents may be done through a parental route such as intravenous injection, intramuscular injection, intra-articular injection, intra-synovial injection, intrathecal injection, intrahepatic injection, intralesional injection or intracranial injection.

The composition of the agents in the present invention may be prepared in a unit dosage form by formulation using a pharmaceutically acceptable carrier and/or excipient, or formulated by containing the composition in a multi-dose container according to methods which may be easily performed by a person with ordinary skill in the art to which the invention pertains, and in a preferred exemplary embodiment, the composition for photodynamic therapy of the present invention may be formulated as a topical administration preparation for photodynamic treatment of cancer and topically administered.

For the light irradiation in the present invention, a laser light may be used, wherein the wavelength of the laser light is between 630 nm and 680 nm.

Another object of the present invention is to provide a detailed composition of therapeutic agents for photodynamic therapy with bioimaging, which includes a methylene blue nanoparticle.

The other objects and advantages of the present invention will be more apparent from the following detailed description, claims and drawings of the invention.

An aspect of the present invention is to provide a methylene blue nanoparticle including a methylene blue-fatty acid complex and an amphiphilic polymer.

The methylene blue nanoparticle of the present invention is composed of only the materials which are clinically available or derived from human bodies.

Methylene blue is a material to be used when chromoendoscopy in which a colorant is applied or injected is performed such that a lesion and the like, which are difficult to observe or invisible, may be readily observed, and a material which is currently clinically used as a part of a test method dyeing such that for example, for a biopsy of a sentinel lymph node, the position thereof may be easily confirmed, or using a colorant solution during endoscopy of the digestive tract.

Methylene blue is a positively charged dye and is in itself very difficult to penetrate into a cell, but forms a stable methylene blue/fatty acid complex with fatty acid by means of electrostatic force and hydrophobic interaction in a molecular structure among the methylene blue nanoparticles of the present invention, thereby exhibiting high solubility to the solvent.

The fatty acid included in the methylene blue nanoparticle of the present invention refers to carboxylic acid or salt thereof, and in an exemplary embodiment, the fatty acid may be a saturated or unsaturated monocarboxylic acid having a long chain shape, and is preferably oleic acid or salt thereof.

The amphiphilic polymer included in the methylene blue nanoparticle of the present invention may be used without limitation as long as the polymer is a polymer in which molecules may be aggregated to form a micelle structure as a compound which has both a hydrophilic portion and a hydrophobic portion. When a polymer micelle is formed in a hydrophilic solvent, the hydrophobic portions of the molecule are aggregated in the core portion to form a nucleus, and the hydrophilic portions form an external portion which is in contact with water. A hydrophobic material such as oil is disposed at an internal portion of the micelle in an aqueous solvent and thus is stabilized and dissolved in the solvent.

In an exemplary embodiment of the present invention, as the amphiphilic polymer, it is possible to use an anionic amphiphilic polymer such as a polymer having a carboxylate, sulfonate or phosphonate structure as a hydrophilic group, a cationic amphiphilic polymer such as a polymer including a quaternary ammonium salt as a hydrophilic group, an amphiphilic polymer having both a portion capable of being anionic and a portion capable of being cationic in a molecule thereof, an amphiphilic polymer having a non-electrolyte as a hydrophilic portion, that is, a hydrophilic portion which is not ionized, and the like, and preferably, a polyoxyethylene-polyoxypropylene block copolymer may be used.

In a preferred exemplary embodiment, the methylene blue-fatty acid complex is enclosed in an amphiphilic polymer micelle in an aqueous environment, and accordingly, nanoparticles of the present invention may be self-assembled.

In an exemplary embodiment, the methylene blue nanoparticle of the present invention may be prepared by a method including: forming a methylene blue-fatty acid mixture by mixing methylene blue with fatty acid, forming a complex by freeze-drying the mixture, and mixing the thus-obtained complex with an amphiphilic polymer, but is not limited to the method.

Another aspect of the present invention is to provide a composition for photodynamic therapy, which includes the aforementioned methylene blue nanoparticle.

The composition for photodynamic therapy of the present invention targets specifically a hyperplasia disease site such as cancer or tumor to exhibit the treatment effect, and a hyperplasic disorder which may be treated by the method of the present invention include, but is not limited to, tumor diseases such as acral lentiginous melanoma, actinic keratosis, adenocarcinoma, adenoid cystic carcinoma, adenoma, adenosarcoma, adenosquamous carcinoma, astrocytic tumors, glucagonoma, hemangioblastoma, hemangioendothelioma, hemangioma, hepatic adenoma, hepatic adenomatosis, hepatocellular carcinoma, insulinoma, interepithelial neoplasia, interepithelial squamous cell neoplasia, invasive squamous cell carcinoma, large cell carcinoma, leiomyosarcoma, lentigo maligna melanoma, malignant melanoma, malignant mesothelioma, medulloblastoma, and medulloepithelioma, and cancer diseases such as pituitary adenoma, neuroglioma, encephalophyma, nasopharyngeal carcinoma, laryngeal cancer, thymoma, mesothelioma, breast cancer, lung cancer, gastric cancer, esophageal cancer, colorectal cancer, hepatoma, pancreatic cancer, intrapancreatic secreting-tumor, gallbladder cancer, penile cancer, ureteral cancer, renal cell carcinoma, prostate cancer, bladder cancer, non-hodgkin's lymphoma, myelodysplastic syndrome, multiple myeloma, plasma cell neoplasm, leukemia, childhood cancers, skin cancer, ovarian cancer, cervical cancer and ocular cancer (ocular melanoma).

The composition of the present invention has an excellent apoptosis-inducing capacity and photo-toxicity specifically against cancer cells, particularly, breast cancer cell, and thus may be preferably used for the treatment of breast cancer. The composition for photodynamic therapy of the present invention may further include a pharmaceutically acceptable carrier, and the pharmaceutically acceptable carrier is one typically used in formulations, and includes, but is not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil and the like. The composition for photodynamic therapy of the present invention may additionally include, in addition to the ingredients, a lubricant, a wetting agent, a sweetener, a flavor, an emulsifier, a suspending agent, a preservative, and the like.

Suitable pharmaceutically acceptable carriers and formulations are described in detail in Remington's Pharmaceutical Sciences (19th ed., 1995).

The composition for photodynamic therapy of the present invention may be prepared in a unit dosage form by formulation using a pharmaceutically acceptable carrier and/or excipient, or formulated by containing the composition in a multi-dose container according to methods which may be easily performed by a person with ordinary skill in the art to which the invention pertains, and in a preferred exemplary embodiment, the composition for photodynamic therapy of the present invention may be formulated as a topical administration preparation for photodynamic treatment of cancer and topically administered.

A suitable administration amount of the composition for photodynamic therapy of the present invention may vary depending on various factors such as formulation method, administration method, age, weight, sex or disease condition of a patient, diet, administration time, administration route, excretion rate and response sensitivity, and an ordinarily skilled physician may easily decide and prescribe an administration amount effective for a desired therapy or prophylaxis. Still another aspect of the present invention relates to a contrast agent composition, which includes the aforementioned methylene blue nanoparticle.

The methylene blue nanoparticle used in the present invention may be used as a contrast agent for image-guided operation, which exactly indicates a resection margin due to excellent topical cancer targeting property and near-infrared fluorescent signal at the time of cancer image diagnosis and cancer operation.

Further, the methylene blue nanoparticle may be used as a phototherapeutic agent which completely cures cancer in a non-operative manner due to excellent topical cancer targeting property and capacity of generating singlet oxygen, or minimizes an operation excision site by reducing the size of cancer tissue.

In addition, the methylene blue nanoparticle exhibits near-infrared fluorescence along with excellent topical cancer targeting property and capacity of generating singlet oxygen, and thus may be used simultaneously for bioimaging diagnoses such as optical imaging, and cancer targeting photodynamic therapy.

The contrast agent composition of the present invention may further include the aforementioned pharmaceutically acceptable carrier, may be parenterally or orally administered in some cases, and may be administered via a parenteral route such as intravenous injection, intramuscular injection, intra-articular injection, intra-synovial injection, intrathecal injection, intrahepatic injection, intralesional injection or intracranial injection.

Since the nanoparticle for use as topical cancer targeting phototherapeutic agent of the present invention is composed of only a material of which the composition is clinically used or derived from human bodies, and thus may be used in human bodies, there is an advantage in that a barrier to clinical entry is low and the possibility of commercialization is very high.

The methylene blue nanoparticle of the present invention has an effect that may be used not only as a contrast agent for image-guided operation, which exactly indicates a resection margin due to excellent topical cancer targeting property and near-infrared fluorescent signal at the time of cancer image diagnosis and cancer operation, but also as a phototherapeutic agent which completely cures cancer in a non-operative manner due to excellent topical cancer targeting property and capacity of generating singlet oxygen, or minimizes an operation excision site by reducing the size of cancer tissue.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The accompanying drawings, which are included to provide a further understanding of the disclosure and are incorporated in and constitute a part of this specification, illustrate exemplary embodiments and together with the description serve to explain the principles of the disclosure.

In the drawings:

FIG. 1 is a schematic view of forming self-assembled nanoparticles including methylene blue as a photosensitizer in water.

FIG. 2a shows the solubility of methylene blue; FIG. 2b is a graph showing the absorbance of an aqueous solution of nanoparticles and methylene blue prepared in Example 1, which is measured by UV-visible spectrometer (Agilent 8453); and FIG. 2c is a graph showing fluorescence wavelength spectra of the aqueous solution, which is measured by fluorescence spectrophotometer (Hitachi F-7000, wavelength calibrated for excitation and emission).

FIG. 3a is a graph showing the size of the nanoparticles prepared in Example 1, which is measured by dynamic light scattering; and FIG. 3b is a photograph of the nanoparticles observed by transmission electron microscope (TEM, CM30, FEI/Philips, 200 kV).

FIG. 4 is a table in which the nanoparticles prepared in Example 1 are measured in terms of the capacity of generating a singlet oxygen in Example 2.

FIG. 5 is fluorescence and optical photographs of each cancer cell in control (CTRL) and after a methylene blue aqueous solution (MB Sol.) and nanoparticles (MB NPs) are injected, which are taken in Example 3 (1). (FIG. 5a—MDA-MB-231; FIG. 5b—MCF-7; FIG. 5c—PC3; FIG. 5d—HeLa; and FIG. 5e—HT-29)

FIG. 6 is fluorescence and optical photographs of each normal cell in a control (CTRL) and after a methylene blue aqueous solution (MB Sol.) and nanoparticles (MB NPs) are injected, which are taken in Example 3 (1). (FIG. 6a—MRC-5; FIG. 6b—Clone 1-5c-4; and FIG. 6c—NIH3T3)

FIG. 7 is graphs of cytotoxicity (Dark) and photo-toxicity (Photo) of nanoparticles for each cancer cell, which are measured in Example 3 (2). (FIG. 7a—MDA-MB-231 cell; FIG. 7b—MCF -7 cell; FIG. 7c—PC-3 cell; FIG. 7d—HeLa cell; and FIG. 7e—HT-29 cell)

FIG. 8 is graphs of cytotoxicity (Dark) and photo-toxicity (Photo) of nanoparticles for each normal cell, which are measured in Example 3 (2). (FIG. 8a—normal cells MRC-5; FIG. 8b—Clone -1-5c-4; and FIG. 8c—NIH3T3)

FIG. 9 shows photographs in which a change in shape of a cell is observed over the time of irradiation of a light source on a HeLa cell into which MB NPs have been injected, which are taken in Example 3 (2).

FIG. 10 is graphs in which the material absorption and apoptosis capacity of each cancer cell into which MB NPs have been injected in Example 3 (3) are measured by fluorescence-activated cell sorter (FACS, EMD Millipore Corporation, USA).

FIG. 11 is graphs in which the material absorption and apoptosis capacity of each normal cell into which MB NPs have been injected in Example 3 (3) are measured by fluorescence-activated cell sorter (FACS, EMD Millipore Corporation, USA).

FIG. 12 is photographs in which capacity of MB NPs and MB Sol. infiltrated into tissue is confirmed in Example 4 (1).

FIG. 13a is a photograph in which image diagnosis behaviors of methylene blue nanoparticles (MB NPs) in an initial cancer model are confirmed by topical cancer targeting contrast in Example 4 (2). FIG. 13b is a photograph showing the image of methylene blue aqueous solution (MB Sol.) after topical administration.

FIG. 14 shows photographs in which the apoptosis capacity of MB NPs and the possibility of photodynamic therapy using an initial cancer model are confirmed in Example 4 (3).

FIG. 15a shows photographs of a cancer site and FIG. 15b is a graph of a change in the size of cancer, of an animal model over time according to the photodynamic therapy, which is prepared in Example 4 (4).

FIG. 16 is a graph in which the body weight of an animal (PDT) which has been subjected to photodynamic therapy is compared with the body weight of a control (Ctrl) which has not been subjected to photodynamic therapy in Example 4 (4).

DETAILED DESCRIPTION OF INVENTION

Description will now be given in detail of the exemplary embodiments, with reference to the accompanying drawings. For the sake of brief description with reference to the drawings, the same or equivalent components will be provided with the same reference numbers, and description thereof will not be repeated.

Hereinafter, the present invention will be described in more detail through the Examples. These Examples are provided only for more specifically describing the present invention, and it will be obvious to a person with ordinary skill in the art to which the present invention pertains that the scope of the present invention is not limited by these Examples.

EXAMPLE

Example 1

Formation of Self-Assembled Nanoparticles Comprising Methylene Blue As Photosensitizer in Aqueous Environment Preparation and Evaluation of Self-assembled Nanoparticles Using Oleate
(1) Hydrophobic Modification of Methylene Blue/Sodium Oleate by Electrostatic Force 20 mg of methylene blue (MB, Aldrich Chemical Co.) and 30 mg of sodium oleate (O, Aldrich Chemical Co.) were dissolved in 100 mL of tetrahydrofuran (THF, Daejung Chemical Industry Co., Ltd.) by heating at 60 to 90° C. for 1 to 5 minutes.

A stable methylene blue/sodium oleate complex (MBO) was formed by electrostatic force and hydrophobic interaction in a molecular structure, thereby exhibiting high solubility to the solvent.

Remnant sodium oleate and other impurities were removed from the MBO solution using a syringe filter (5 μm), and then MBO was obtained by the following freeze-drying.
(2) Preparation and Evaluation of Nanoparticle Comprising MBO and Amphiphilic Polymer 0.2 mg of MBO obtained in (1) and 20 mg of an amphiphilic polymer Pluronic® F-68 (purchased from Aldrich Chemical Co.) were added into THF solvent and sufficiently mixed, and then the solvent was completely removed. The mixture from which the solvent had been completely removed was uniformly dispersed in 2 ml of water to prepare methylene blue nanoparticles (MB NPs).

The absorbance and fluorescence of methylene blue dissolved in water (MB Sol.) and methylene blue nanoparticles dispersed in water (MB NPs) were measured, and the results were as shown in FIGS. 2b and 2c, respectively. It can be confirmed from FIGS. 2b and 2c that due to the formation of nanoparticles, the absorption wavelength and fluorescent wavelength of MB NPs were shifted to a short wavelength region compared to MB dissolved in water.

The size of the nanoparticles was measured by Zetasiser-nano ZS (Malvern Instruments, UK) and the shape of the nanoparticles was observed by transmission electron microscope (TEM, CM30, PEI/Philips, 200 kV). The results were represented in FIGS. 3a and 3b, respectively. As can be confirmed from FIGS. 3a and 3b, the nanoparticle was observed to have a spherical form with a diameter of 80 to 100 nm.

Preparation of Self-assembled Nanoparticles Using Stearate
(1) Hydrophobic Modification of Methylene Blue/Sodium Stearate by Electrostatic Force As a comparative example, a mixture of methylene blue and sodium stearate (MBSt) was prepared in the same way as mentioned above, except using 30 mg of sodium stearate (St, purchased from Aldrich Chemical Co.) instead of sodium oleate.

Although the combination of methylene blue and sodium oleate was completely dissolved in the solvent, the combination of a methylene blue and sodium stearate showed very low solubility to the solvent because sodium stearate was not dissolved in the solvent and thereby failed to modify methylene blue (see FIG. 2a).
(2) Preparation of Nanoparticle Comprising MBSt and Amphiphilic Polymer An experiment was carried out to prepare methylene blue nanoparticles under the same condition using MBSt and 20 mg of an amphiphilic polymer Pluronic® F-68 (Aldrich) in THF solvent. However, no stable methylene blue nanoparticle was obtained in the solvent because MBSt itself failed to form a stable complex in the solvent.

It was confirmed from Example 1 that methylene blue can be efficiently enclosed within amphiphilic polymers in aqueous environment by electrostatically neutralizing and hydrophobically modifying methylene blue using fatty acid. The nanoparticles in which methylene blue is enclosed within amphiphilic polymers were found to have excellent structure stability maintaining their particle state through the size measurement and shape observation.

Example 2

Evaluation of Capacity of Generating Singlet Oxygen of Self-Assembled Nanoparticles (MB NPs) Comprising Methylene Blue As Photosensitizer in Aqueous Environment In order to use MB NPs dispersed in water as a photosensitizer for photodynamic therapy, the capacity of generating a singlet oxygen of the nanoparticles according to the laser irradiation was determined and compared to that of MB dissolved in water (MB Sol.). A laser with a wavelength of 655 nm which is known to be capable of producing a singlet oxygen (Chanchun New industries Optoelectronics Tech. Co., Ltd., ex=655 nm, 200 mW output power) was used.

The amount of a singlet oxygen produced was measured by a chemical method using N,N-Dimethyl-4-nitrosoaniline (Aldrich) which is combined with a singlet oxygen to lose the inherent OD max value.

FIG. 4 illustrates the result, confirming that MB NPs showed a capacity of generating singlet oxygen, which is equivalent to that of MB Sol. at 37° C., which is a temperature suitable for living organisms.

By confirming the capacity of generating a singlet oxygen at 37° C., the possibility of photodynamic therapy of methylene blue as a photosensitizer in vivo was confirmed.

Example 3

Evaluation of Cancer Cell Accumulation and Characteristics of Self-Assembled Nanoparticles Comprising Methylene Blue As Photosensitizer in Aqueous Environment (1) Evaluation of Accumulation of MB NPs in Cancer Cell
In order to determine if the nanoparticles (MB NPs) prepared in Example 1 would be accumulated in the cancer cell, $1 \times 10^5$ of each of cancer cells MDA-MB-231 (breast, mammary gland/human, Korean Cell Line Bank), MCF-7 (breast, mammary gland/human, Korean Cell Line Bank), PC-3 (prostate; grade 4; metastasis to bone/human, Korean Cell Line Bank), HeLa (cervix/human, Korean Cell Line Bank), and HT-29 (Colon/human, Korean Cell Line Bank) was respectively dispersed in 2 mL of cell culture solution [DMEM (WELGENE) culture solution was used for the HeLa cell, and RPMI1640 (WELGENE) culture solution was used for the other cells]. And then the solution was put into a dish for cell culture (35 mm, glass-bottomed dish), and cultured in a culture chamber (5% $CO_2$, 37° C.). After 24 hours, the dish was washed with 2 mL of DPBS (WELGENE), and 1.8 mL of the culture solution and 0.2 mL of the nanoparticles were added thereto, and the resulting dish was stored in a culture chamber (5% $CO_2$, 37° C.) for 1 hour. The stored cell culture dish was washed with 2 mL of DPBS, cells were fixed with 1 mL of a cell fixation solution, and then fluorescence images were observed by fluorescence microscope (LEICA DMI3000B equipped with a Nuance FX multispectral imaging system, CRI).

For a comparative experiment, the same experiment was carried out by using a solution (MB Sol.) obtained by dissolving the same amount of MB used in the aforementioned experiment in water. The experimental results for MB NPs and MB Sol. are illustrated in FIGS. 5a to 5e.

Further, in order to check if MB NPs would be accumulated in normal cells other than the cancer cells, experiment was carried out under the same condition regarding MRC-5 (lung/human, Korean Cell Line Bank), clone 1-5c-4(conjunctiva/human, Korean Cell Line Bank), and NIH/3T3 (embryo/mouse, Korean Cell Line Bank) cells, and the results are shown in FIGS. 6a to 6c.

As a result of the experiment, the MB Sol. had so low infiltration capacity into cell that MB Sol. was not found in the cell, whereas the MB NPs which formed nanoparticles in an aqueous environment due to hydrophobic modification of methylene blue using a fatty acid salt and an amphiphilic polymer were found to have improved infiltration capacity and nanoparticle stability in the cell ambient environment.

(2) Evaluation of Cancer Cell Photo-Toxicity of MB NPs

In order to confirm of the cytotoxicity of MB NPs, 200 μL of a cell culture solution in which $1 \times 10^4$ ea of cells were dispersed was put into a dish for cell culture (96-well plate) and cultured (5% $CO_2$, 37° C.) in an artificial culture chamber for 24 hours, and the dish was washed with DPBS, and then a mixture solution of 20 μL of MB NPs and 180 μL of a cell culture solution was added to the cell, and the resulting culture solution was cultured in the same artificial culture chamber for 1 hour. After the dish was washed with DPBS, the number of each cell was observed by the MTT analysis method.

Further, in order to evaluate the photo-toxicity of MB NPs for each cancer cell, an experiment was performed in the same manner as mentioned above, and the number of cells by photo-toxicity was determined by irradiating laser onto each cell for 20 minutes, and then performing an MTT analysis.

The experiment was performed on cancer cells and normal cells, and MDA-MB-231 cell, MCF-7 cell, PC-3 cell, HeLa cell, and HT-29 cell are illustrated in FIGS. 7a, 7b, 7c, 7d, and 7e, respectively, and normal cells MRC-5, Clone-1-5c-4, and NIH3T3 are illustrated in FIGS. 8a to 8c, respectively.

The experiment of evaluating cytotoxicity and photo-toxicity by MB Sol. was also performed in the same manner as described above, but cytotoxicity and photo-toxicity for a control were also almost the same as described above, so that it was confirmed that there is no cytotoxicity of the material itself, nor cytotoxicity by a light source.

In order to observe the change in cell form over time due to the toxicity by a light source, a culture solution in which $1 \times 10^5$ ea of cells were dispersed was put into a dish for culture (35 mm), and after 24 hours, the dish was washed with 2 mL of DPBS to inject 1.8 mL of the culture solution and 0.2 mL of the prepared MB NPs into the dish. Then, after 1 hour, the sample was observed by a microscope (LEICA DMI3000B equipped with a Nuance FX multispectral imaging system, CRI) along with irradiation of a light source, and the result is shown in FIG. 9.

Through the experiment, it was found that even though nanoparticles with improved infiltration capacity were absorbed in the cell, the cytotoxicity of the material was not significant for each cell, whereas for the cancer cell in which the nanoparticles were absorbed, photo-toxicity by a light source was mostly observed, and it was found that specifically for the breast cancer cells (MDA-MB-231 and MCF-7), the effect was still excellent. As described above, the possibility of cancer cell targeting therapy was confirmed.

(3) Evaluation of Apoptosis-Inducing Capacity of MB NPs Accumulated in Cancer Cell by Laser In order to evaluate the apoptosis-inducing capacity of MB NPs by a light source, 2 mL of a cell culture solution in which $2 \times 10^5$ ea of cells were dispersed was put into a dish for cell culture (12-well plate) and cultured (5% $CO_2$, 37° C.) in an artificial culture chamber for 48 hours. After washing with 2 mL of DPBS, a mixture solution of 1.8 mL of the culture solution and 0.2 mL was injected into the dish for cell culture, and then cultured in an artificial culture chamber for 1 hour to absorb the material. Then, after washing with DPBS, irradiation was performed by a light source using laser with a wavelength of 655 nm for 5 minutes, DPBS was removed, and then a mixture solution Annexin V/FITC of 0.5 mL of a binding buffer and 10 μL of FITC was injected into the dish, and the resulting dish was stored in an artificial culture chamber for 5 minutes. After washing with DPBS, the dish was treated with trypsin EDTA (WELGENE) to separate cells from the dish for cell culture. The separated cells were dispersed in 1 mL of DPBS to perform measurement by a fluorescence-activated cell sorter (FACS, guava easyCyte™Single Sample Flow Cytometer, EMD Millipore Corporation, USA) device.

MB NPs were absorbed in Example 3 (3), an effective apoptosis-inducing capacity could be confirmed from most of the cancer cells through the measurement of the apoptosis-inducing capacity by Annexin V/FITC from the cancer cell irradiated by laser, and it was confirmed that this was a result having the same aspect when compared to the cell photo-toxicity in Example 3 (2). Furthermore, it was confirmed that specifically for the breast cancer cells (MDA-MB-231 and MCF-7) among the cancer cells, the apoptosis-inducing capacity and the photo-toxicity in Example 3 (2) were excellent, and through this, the possibility of a specific cancer cell targeted therapy could be confirmed. The results in Example 3 (3) were illustrated in FIGS. 10 and 11, and from this, the apoptosis-inducing capacities of the cancer cells and the normal cells could be respectively confirmed.

Example 4

Evaluation of Cancer Targeting Accumulation and Characteristics of MB NPs after Being Topically Injected into Living Organism (1) Evaluation of Tissue Infiltration Capacity of MP NPs and MB Sol.

Commercially available chicken breast meat (Moguchon Co., Ltd.) was cut into a predetermined size (3 cm×3 cm×3 cm), 0.5 mL of each of the MB NPs and MB Sol. prepared in Example 1 was applied onto the meat, and then the resulting sample was stored at 37° C. in a water bath. Thereafter, the sample was sufficiently washed with DPBS, and a fluorescence image was obtained by a fluorescence image device 12-bit CCD camera (Kodak Image Station 4000 MM, ex: 625 nm/em: 700 nm). The result is illustrated in FIG. 12.

Since methylene blue is present in the form of nanoparticles embedded in the amphiphilic polymer, it was confirmed that tissue infiltration capacity had been significantly improved compared to methylene blue alone.

(2) Evaluation of MB NPs for Topical Cancer Targeting in Imaging Diagnosis Using Cancer Model 60 μL of a culture solution in which $1\times10^7$ ea of the MDA-MB-231 cells were dispersed was injected into the left hip muscular site of a female rat (Balb/c-nu, 5.5-week old, Orient Bio Inc.). Thereafter, the growth of the cancer tissue for 4 to 5 weeks was confirmed by the naked eye, 60 μL of nanoparticles (MB NPs) in which methylene blue was enclosed were topically injected into the cancer tissue site, and it was confirmed that the cancer tissue target had been accumulated by using a fluorescence image device (IVIS-Spectrum, Perkin-Elmer, USA). For a comparative experiment of the aforementioned experiment, an experiment using a methylene blue aqueous solution (MB Sol.) was carried out on an animal model prepared in the same manner as mentioned above and the results are as illustrated in FIGS. 13a and 13b.

From the experiment, the cancer tissue targeting accumulation capacity of MB NPs was confirmed in the animal cancer model as well, and thereby the possibility of cancer targeting of MB NPs for in vivo imaging diagnosis of cancer was confirmed.

(3) Evaluation of Accumulation and Photo Therapy Characteristics of MB NPs Using Initial Cancer Model In order to perform an accumulation test for nanoparticles in an initial cancer model, $1\times10^6$ ea of SCC7 (Squamous Cell Carcinoma) cells dispersed in 60 μL of the cell culture solution were subcutaneously injected into each of the left and right hip muscular sites of a male rat (Balb/c-nu, 5.5 week-old, Orient Bio Inc.). After 2 hours, 60 μL of MB NPs were subcutaneously injected into the left site where the cancer cell had been injected, and after 2 hours, the material was sufficiently absorbed into the cell, and then laser was irradiated onto the left hip site for 20 minutes. Thereafter, 60 μL of Annexin V/FITC (a mixture solution of 100 μL of a binding buffer and 10 μL of FITC) was subcutaneously injected into the left and right initial cancer sites to evaluate the apoptosis capacity, and a fluorescence image was obtained from the initial cancer model using a fluorescence image device (IVIS-Spectrum, Perkin-Elmer, USA) to evaluate the apoptosis capacity of MB NPs by phototoxicity. The results are illustrated in FIG. 14.

From the experiment, it was confirmed that MB NPs in which hydrophobically modified methylene blue is introduced into the amphiphilic polymer as a photosensitizer could be used to cause apoptosis, and thereby in vivo photodynamic therapy was feasible.

(4) Evaluation of Photodynamic Therapy Efficacy and Biotoxicity of In Vivo MB NPs In order to evaluate an in vivo photodynamic therapy efficacy, 60 μL of a culture solution in which $1\times10^7$ ea of the MDA-MB-231 cell expected to have an excellent photodynamic therapy effect by MB NPs as confirmed in Example 3 (2) was dispersed was injected into the left hip muscular site of a female rat (Balb/c-nu, 5.5-week old, Orient Bio Inc.), the growth of the cancer tissue for 4 to 5 weeks was confirmed by the naked eye, and then 60 μL of MB NPs were subcutaneously injected into the cancer tissue site. Thereafter, the photodynamic therapy (irradiation of laser with a wavelength of 655 nm for 10 minutes) was performed 8 times in total at the interval of 2 to 3 days, the result observed for 28 days is illustrated in FIG. 15a, and the change in the size of cancer (=short axis$^2$×long axis) over a passage of time is illustrated in FIG. 15b.

Furthermore, in order to evaluate the in vivo toxicity of MB NPs, a graph, which compares the weights of a control (Ctrl) which was not subjected to photodynamic therapy and an experimental group (PDT) which was subjected to photodynamic therapy, is illustrated in FIG. 16.

From the experiment, an excellent therapeutic effect was confirmed during the photodynamic therapy using MB NPs as a photosensitizer, and it could be confirmed that the in vivo toxicity of MB NPs by a cancer ambient topical injection was not shown.

The foregoing embodiments and advantages are merely exemplary and are not to be considered as limiting the present invention. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

The invention claimed is:

1. A method for treating of cancer using methylene blue nanoparticles, the method comprising steps of:
   a) administrating a therapeutic agent containing the methylene blue nanoparticles into a tissue;
   b) applying light irradiation to the tissue;
   c) generating a singlet oxygen from the methylene blue nanoparticles; and
   d) inducing cell apoptosis and reducing cancer area,
   wherein each of the methylene blue nanoparticles comprises a methylene blue-fatty acid complex and an amphiphilic copolymer of pluronic F-68,
   wherein the amphiphilic copolymer comprises a polyoxyethylenepolyoxypropylene-polyoxyethylene block copolymer;
   the methylene blue-fatty acid complex is enclosed in a micelle formed by the amphiphilic copolymer; and
   each of the methylene blue nanoparticles has a diameter of 80 to 100 nm and is self-assembled in an aqueous environment.

2. The method of claim 1, wherein fatty acid of the methylene blue-fatty acid complex is oleic acid or salt thereof.

3. The method of claim 1, wherein the amphiphilic copolymer is directly bonded to the methylene blue-fatty acid complex.

4. The method of claim 1, wherein each of the methylene blue nanoparticles consists of a methylene blue-fatty acid complex and an amphiphilic copolymer.

5. The method of claim 1, wherein the administrating therapeutic agent is done through any one route selected from the group consisting of intravenous injection, intramuscular injection, intra-articular injection, intra-synovial injection, intrathecal injection, intrahepatic injection, intralesional injection, and intracranial injection.

6. The method of claim 1, the light irradiation is achieved by a laser light, wherein a wavelength of the laser light is between 630 nm and 680 nm.

7. The method of claim 1, wherein the treating of the cancer is achieved by photodynamic therapy using the methylene blue nanoparticles as a photodynamic agent.

8. The method of claim 1, wherein the methylene blue nanoparticles form a mixture with a pharmaceutically acceptable carrier.

9. The method of claim 8, wherein the pharmaceutically acceptable carrier is selected from the group consisting of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil.

10. The method of claim 1, wherein the cancer is a breast cancer.

* * * * *